US00PP37667P2

(12) United States Plant Patent
Hansoti

(10) Patent No.: US PP37,667 P2
(45) Date of Patent: Sep. 1, 2026

(54) ***SANSEVIERIA* PLANT NAMED 'Hansoti61'**

(50) Latin Name: ***Sansevieria* hybrid**
Varietal Denomination: Hansoti61

(71) Applicant: Ashish Hansoti, Mumbai (IN)

(72) Inventor: Ashish Hansoti, Mumbai (IN)

( * ) Notice: Subject to any disclaimer, the term of this patent is extended or adjusted under 35 U.S.C. 154(b) by 0 days.

(21) Appl. No.: 19/349,641

(22) Filed: Oct. 3, 2025

(51) Int. Cl.
*A01H 6/12* (2018.01)
*A01H 5/12* (2018.01)

(52) U.S. Cl.
USPC ..... Plt./382

(58) Field of Classification Search
USPC ..... Plt./382
CPC ..... A01H 6/12; A01H 5/12
See application file for complete search history.

*Primary Examiner* — Keith O. Robinson

(57) ABSTRACT

A new and distinct cultivar of *Sansevieria* plant named 'HANSOTI61' is disclosed, characterized by a unique compact plant form with thick, fleshy leaves held in a stiff upright rosette. The stiff leaves are fleshy, with maximum cross-sectional width 1.5 to 1.7 cm, upright, very stiff but with relatively non-aggressive tips. Overall, 'Hansoti61' presents as a compact silvery grey-green, stiff, vertical rosetted pot plant with contrasting bands of dark green. 'Hansoti61', unlike most commercial *Sansevieria* cultivars, comes true and quickly gives adventitious shoots from leaf cuttings and the resulting pups can be used in various size pots. 'Hansoti61' is an extremely tough plant, when compared to other *Sansevieria* cultivars, with practically no pests or disease problems and very long lasting under low light indoor conditions. The new variety is a *Sansevieria*, typically produced as an ornamental plant.

8 Drawing Sheets

Latin name of the genus and species: *Sansevieria* hybrid. Cultivar denomination: 'HANSOTI61'.

BACKGROUND OF THE INVENTION

The present invention relates to a new and distinct cultivar of *Sansevieria* plant, botanically known as *Sansevieria* hybrid of the family Asparagaceae, hereinafter referred to by the cultivar name 'HANSOTI61'.

*Sansevieria* is a monocotyledonous plant with fleshy, succulent leaves which are available in a huge range of species, varieties and cultivars as an outdoor ornamental plant (under tropical or warm temperate conditions) or as indoor plants. The new cultivar 'Hansoti61' is considered a cultivar of *Sansevieria* in the group denominated as "Novelty *Sansevieria* Group" as in it is not one of the *Sansevieria trifasciata* species.

The new *Sansevieria* 'Hansoti61' was discovered and selected by Mr. Ashish Hansoti, as a chance seedling resulting from the open-pollination of an unpatented hybrid *Sansevieria* in the breeder's collection known as *Sansevieria* 'Hedgehog', a Thai *Sansevieria* hybrid of *Sansevieria cylindrica* parentage but unusual in having a regular rosette rather than typical flat, two-dimensional fan-like (Distichous) leaf arrangement of the *S. cyclindrica* species and hybrids. The pollen parent is unknown (open-pollination). The breeder speculates that the pollen parent is *Sansevieria* hybrid 'Silver Steel' which was flowering nearby, at Village Asle, District Satara, Maharashtra State in Western India sometime in March 2022. The new *Sansevieria* 'HANSOTI61' was discovered and selected by the inventor, Ashish Hansoti, during the Fall of 2022.

Asexual reproduction of the new *Sansevieria* cultivar by vegetative side shoots (pups) as well as leaf cuttings was first performed in November 2022 in Village Asle, District Satara, Maharashtra State in Western India and it was seen that the distinctive combination of characteristics of the new cultivar reproduced true to type from basal suckers as well as from the leaves.

BRIEF SUMMARY OF THE INVENTION

The following traits have been repeatedly observed and are determined to be unique characteristics of 'HANSOTI61', which in combination distinguish this *Sansevieria* as a new and distinct cultivar:

1. Unique compact plant form with thick, fleshy leaves held in a stiff upright rosette.
2. Light silver grey-green foliage with distinct, contrasting dark green linear markings in the form of annular rings around each leaf-a form of transverse cross hatching, contrasting with the light silvery grey-green background. Overall, 'Hansoti 61' presents as a compact silvery grey-green, stiff, vertical rosetted pot plant with contrasting bands of dark green.
3. The stiff leaves are fleshy, with maximum cross-sectional width 1.5 to 1.7 cm, upright, very stiff but with relatively non-aggressive tips.
4. 'Hansoti61', unlike most commercial *Sansevieria* cultivars, comes true and quickly gives adventitious shoots from leaf cuttings and the resulting pups can be used in various size pots.
5. Leaves are small in pups and get bigger with age. Leaves in plants grown in 9 cm pot would be 7-8 cm long giving a rosette diameter of 9 to 10 cm. About 15-18 leaves per plant, increasing in number with plant age.
6. 'Hansoti61' is an extremely tough plant, when compared to other *Sansevieria* cultivars, with practically no pests or disease problems and very long lasting under low light indoor conditions.

The new cultivar has an upright growth habit and the entire plant can reach a height range between 8 and 9 cm when grown in a 9 cm pot. The plant can get larger with age and in larger pots, with the oldest plants observed up to 15 cm tall. The leaves are fleshy and seem cylindrical with maximum width of 1.7 cm and lanceolate with a smooth texture and waxy feel. Seen from the top, the blades are distinctly thick or fleshy with a deep sulcus. This cultivar also has a rosette that is an inverted triangle shape like most *Sansevieria*.

The new cultivar presents with 15-18 leaves per plant when it reaches sale size (between 2-4 months from rooted pups depending on finished pot size).

The new cultivar is very drought tolerant and adapts well to conditions of bright light and heavy shade (exterior and interior).

The base color of a recently mature leaf is a silvery grey-green near 191B or 191C with darker lines and annular cross hatching which is near 139A. With age the base leaf colour darkens slightly so near 138A. The main colour of a recently mature leaf of lower surface is a grey-green near 190A with darker lines and annular cross hatching which is near 139A.

PARENTAL COMPARISON

Plants of the new *Sansevieria* 'HANSOTI61' are similar to plants of the parental cultivar, however, 'HANSOTI61' differs in the characteristics described in Table I.

TABLE I

Comparison of Seed Parent *Sansevieria* 'Hedgehog' & New cultivar 'Hansoti61'

| | Characteristic | *Sansevieria* 'Hedgehog' | New cultivar 'Hansoti61' |
|---|---|---|---|
| 1. | Leaf Habit | 'Hedgehog' has fleshy, terete leaves without a distinct sulcus or groove along the length | 'HANSOTI61' has less fleshy, narrower leaves with a wide sulcus. |
| 2. | Leaf Colour | Overall coloration is grey green without annular cross hatching but with short linear darker lines. | Overall coloration is a much lighter, Silver Grey-green with very prominent, dark green narrow annular rings - cross hatching. |
| 3. | Leaf size & Shape | Leaves are wider, somewhat longer and a little more recumbent. | Leaves are more fleshy and more upright. |
| 4. | Plant Vigour | Somewhat less vigorous, giving pups slower from leaf cuttings and slower subsequent growth. The fleshier plant takes longer to fill up. | Somewhat more vigorous, giving pups from leaf cuttings faster and also faster subsequent growth than the seed parent. |

COMMERCIAL COMPARATOR

Plants of the new *Sansevieria* 'HANSOTI61' are similar to the commercial cultivar *Sansevieria* 'HANSOTI26', U.S. Plant Pat. No. 33,149. Plants of the new *Sansevieria* 'HANSOTI61' differ from plants of the commercial cultivar in the characteristics described in Table II.

TABLE II

Comparison of similar *Sansevieria* cultivar 'HANSOTI26' and the new cultivar 'HANSOTI61'

| | Characteristic | *Sansevieria* 'Hansoti26' U.S. Plant Pat. No, 33,149 | New cultivar 'Hansoti61' |
|---|---|---|---|
| 1. | Leaf Habit & number | 'Hansoti26' has much flatter leaves. Number of leaves is 10-12, fewer than 'Hansoti61' | Much more terete leaves almost circular in cross section with a prominent sulcus along most of the length of the leaf. Number of leaves is 15-18, more leaves than in 'Hansoti26' |
| 2. | Leaf Colour | Background leaf coloration is green rather than silvery grey-green with distinct cross hatching and prominent linear lines and markings. | Overall coloration is much lighter silvery Grey-green with distinct circular green rings around the leaf and no linear lines. |
| 3. | Leaf size & morphology | Leaves are much longer and more recumbent. Each leaf curves gently outwards. Leaf width is 15 to 20 mm. The channel is very open, & runs the whole length of the leaf. | Leaves are shorter and more upright. Individual leaf is almost straight. Leaf diameter is around 15 to 17 mm. The channel or sulcus is deep and present along most of the length of the leaf. |
| 4. | Plant Growth Habit | 'Hansoti26' is wider growing but less substantial, with thinner leaves and is best presented as a multi-plant per pot, typically 3 plants per pot. | 'Hansoti61' is a shorter, chunkier plant with fat, fleshy leaves that fill the pot using only 1 plant per pot. |
| 5. | Plant Vigour | Somewhat more vigorous, giving pups from leaf cuttings quicker and faster subsequent growth. | Somewhat less vigorous, taking longer to give pups from leaf cuttings and slower subsequent growth. |

BRIEF DESCRIPTION OF THE PHOTOGRAPHS

The accompanying photographs illustrate the overall appearance of the new *Sansevieria* cultivar 'HANSOTI61' showing the colors as true as is reasonably possible with colored reproductions of this type. Colors in the photographs may differ slightly from the color value cited in the detailed botanical description which accurately describe the color of 'HANSOTI61'.

These pictures illustrate the plant form which is the unique characteristic of 'HANSOTI61' and at the same time demonstrates comparisons with both the parent cultivar and the comparator 'Hansoti26'. All plants were grown in an open poly house (high tunnel) at Village Asle, District Satara, Maharashtra State in Western India. Average temperature in Asle is 25° C. with summer highs of 39° C. and winter lows of 6° C. Plants grow under natural light conditions and between 30% to 75% shade levels depending on the season (higher shade in hot summer conditions). These conditions closely approximate those used in commercial practice in India.

Figure 1:
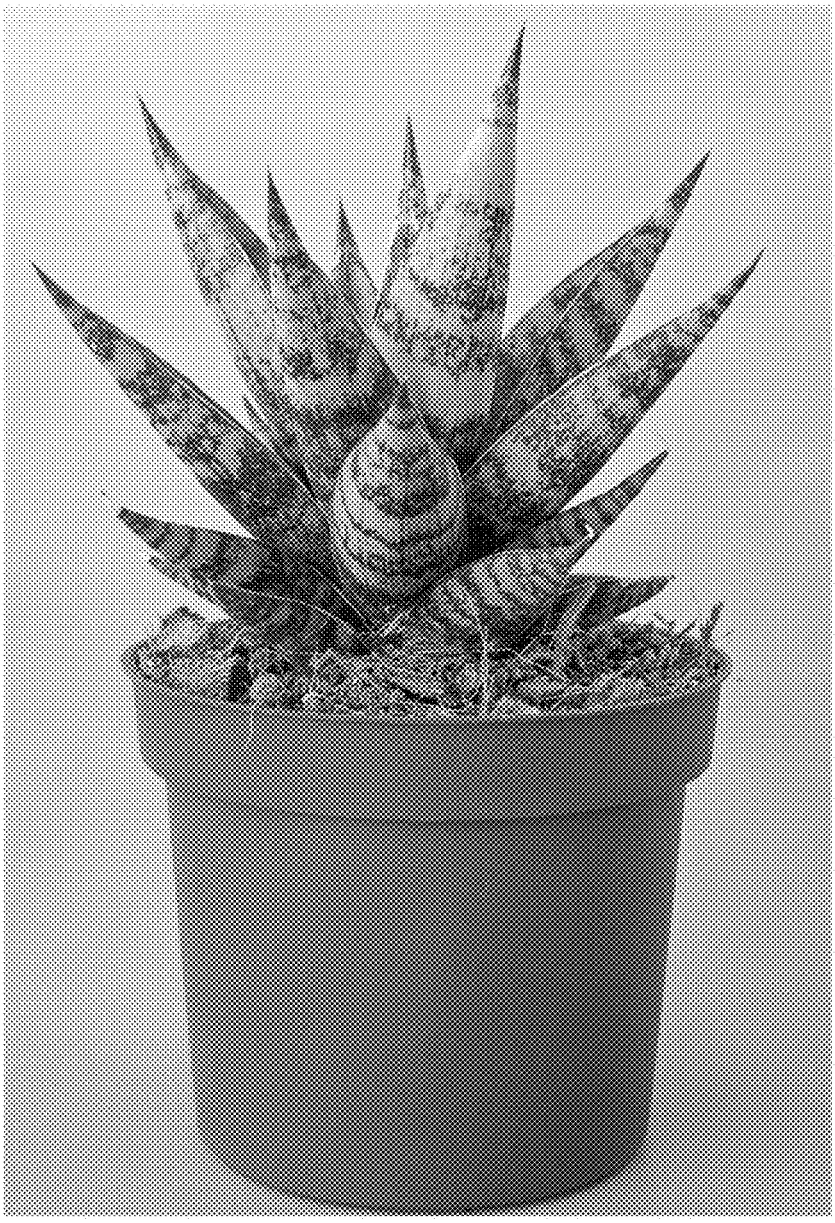
FIG. 1 illustrates a side view of *Sansevieria* 'HANSOTI61' in a 9 cm pot. This plant is 3 to 4 months old from a rooted cutting.
Figure 2:
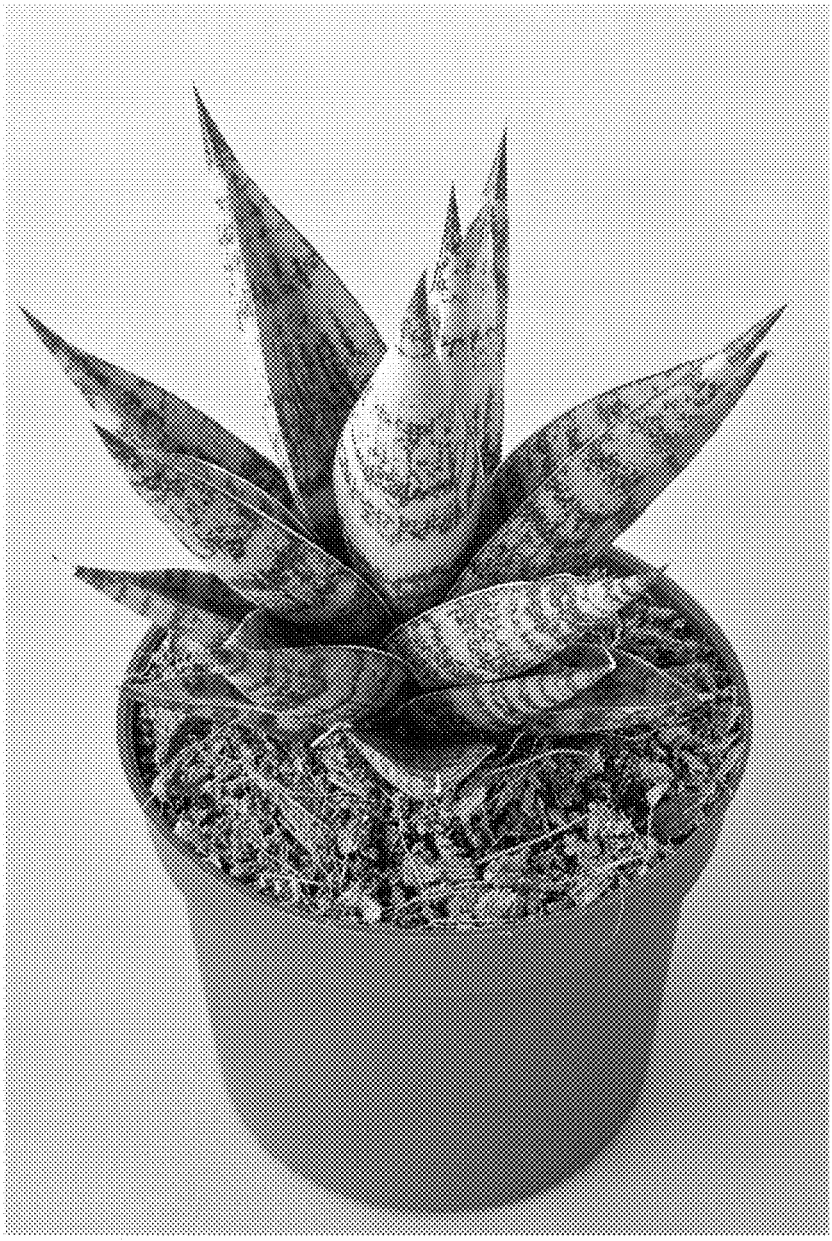
FIG. 2 illustrates the same plant as FIG. 1 from a view of about 45° from above.
Figure 3:
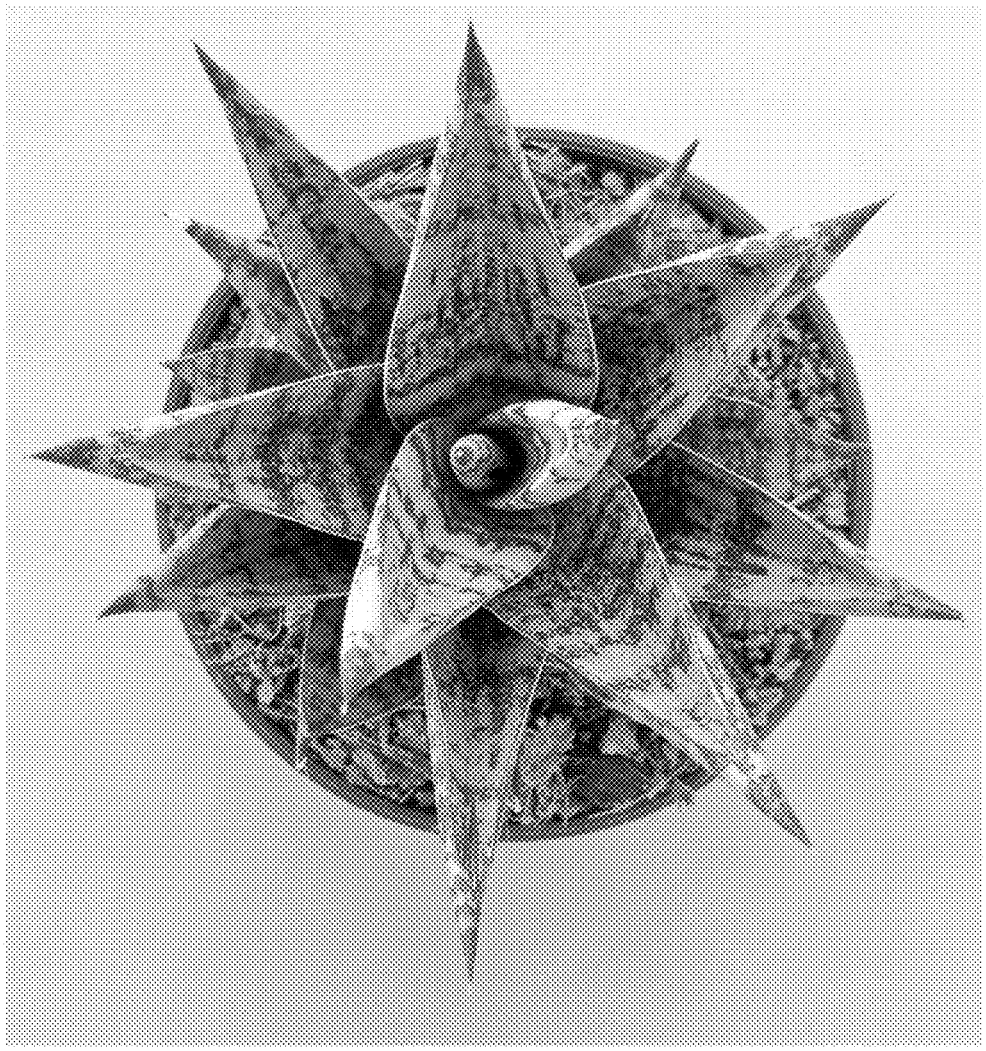
FIG. 3 illustrates the same plant as FIG. 1 and FIG. 2 from a top-down view.
Figure 4:
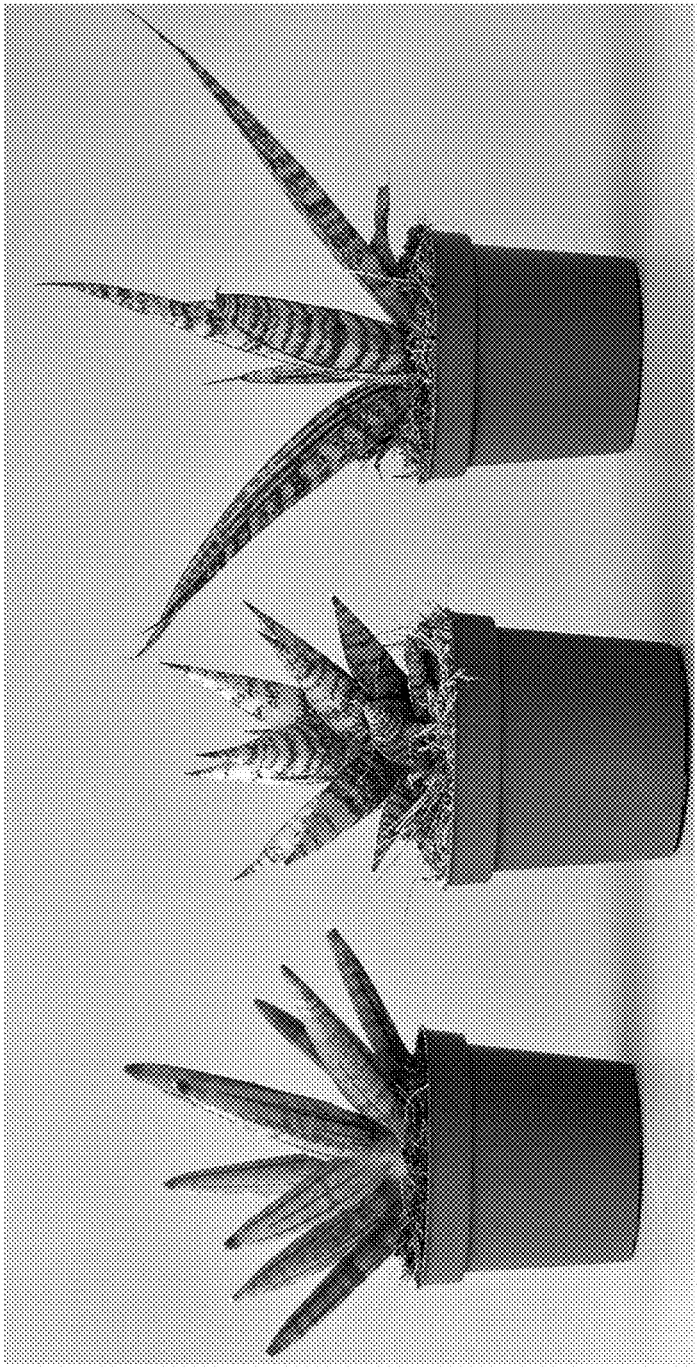

FIG. 4: is a comparison of a plant of 'HANSOTI61' (center) with the parent cultivar, 'Hedgehog' (left) and comparator 'Hansoti26' (right). All plants are 3 to 4 months old from a rooted cutting. This photograph was taken from a side view.

Figure 5:
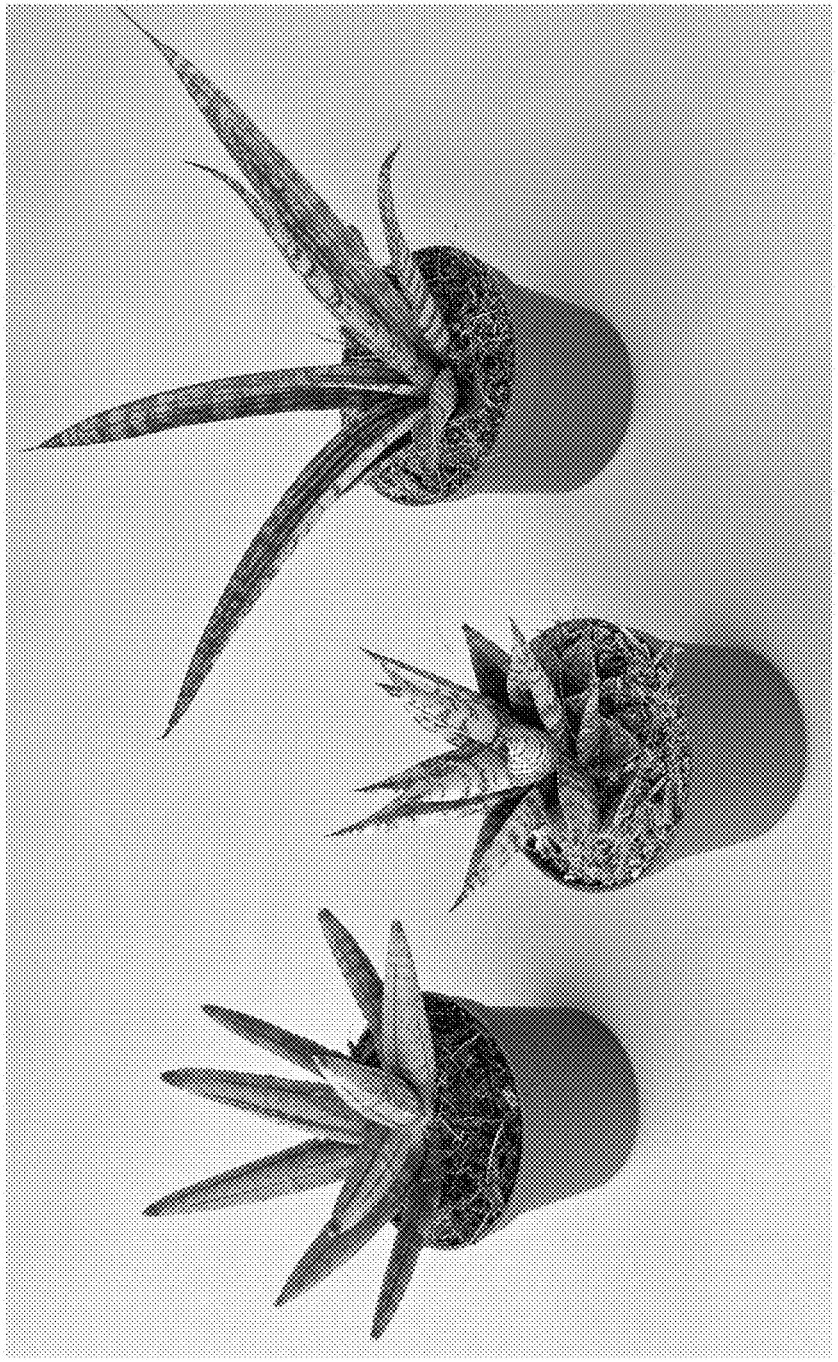

FIG. 5: is a comparison of a plant of 'HANSOTI61' (center) with the parent cultivar, 'Hedgehog' (left) and comparator 'Hansoti26' (right). All plants are 3 to 4 months old from a rooted cutting. This photograph was taken from a view of about 45° from above.

Figure 6:
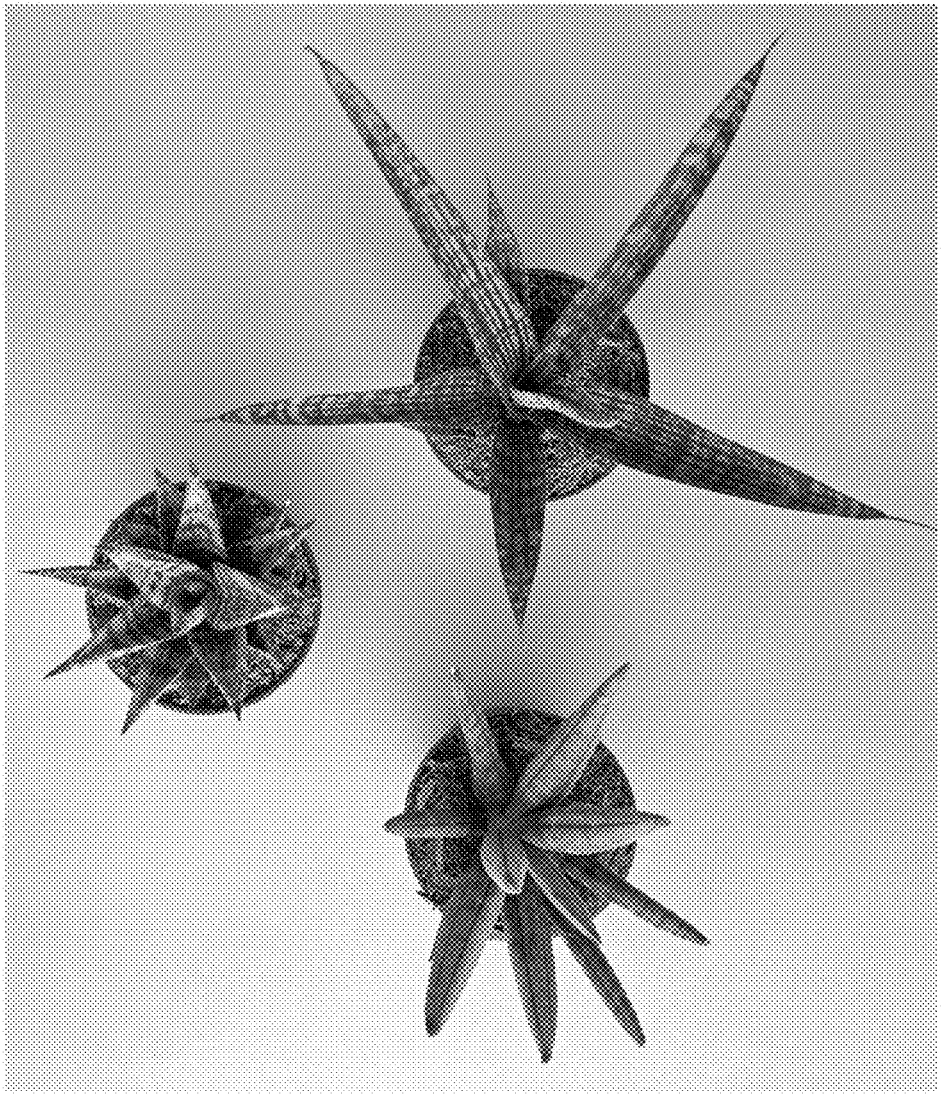

FIG. 6: is a comparison of a plant of 'HANSOTI61' (center) with the parent cultivar, 'Hedgehog' (left) and comparator 'Hansoti26' (right). All plants are 3 to 4 months old from a rooted cutting. This photograph was taken from a top-down view.

Figure 7:
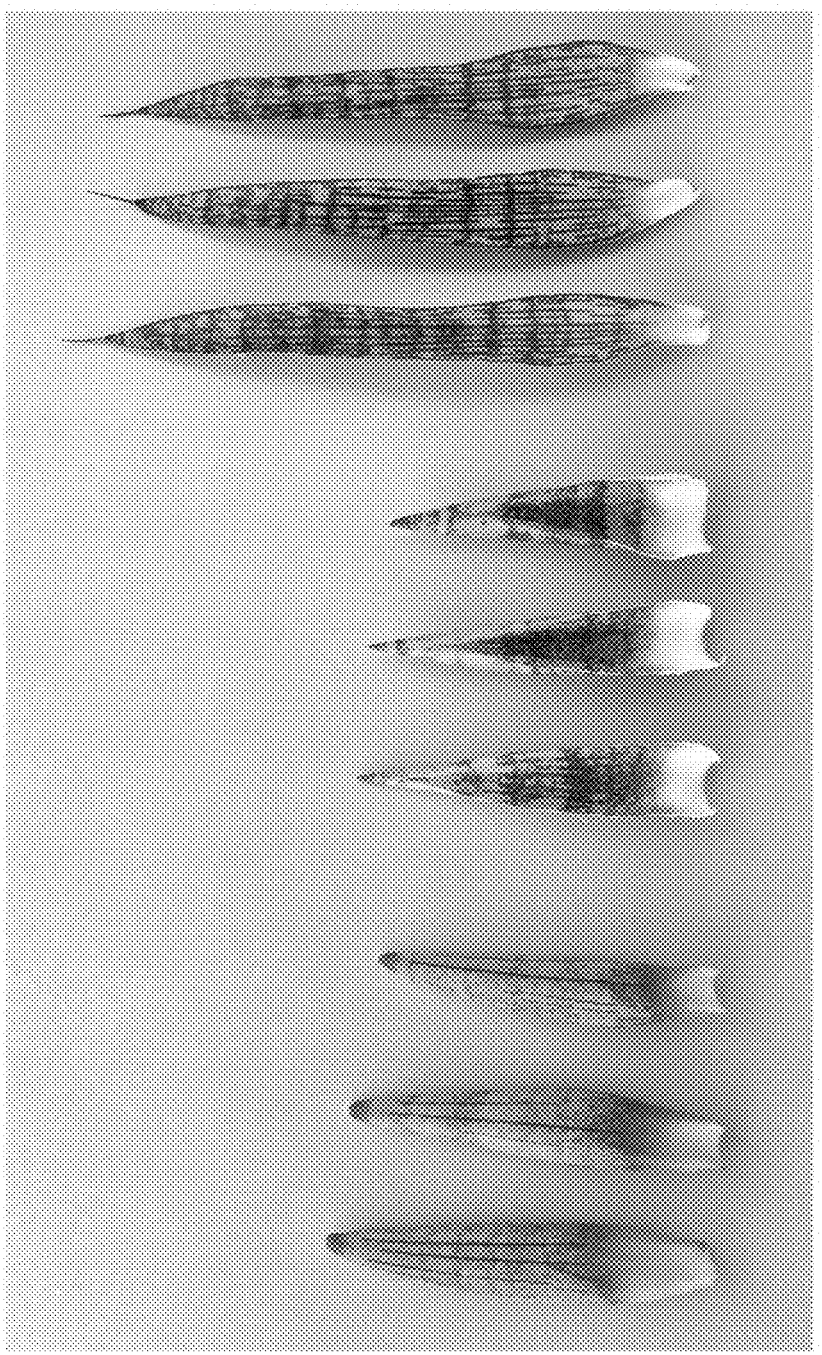

FIG. 7: Shows a comparison of adaxial leaf surfaces of 'HANSOTI61' (center) with the parent cultivar, 'Hedgehog' (left) and comparator 'Hansoti26' (right), illustrating comparative size, shape, colour, cross hatching pattern and sulcus.

Figure 8:
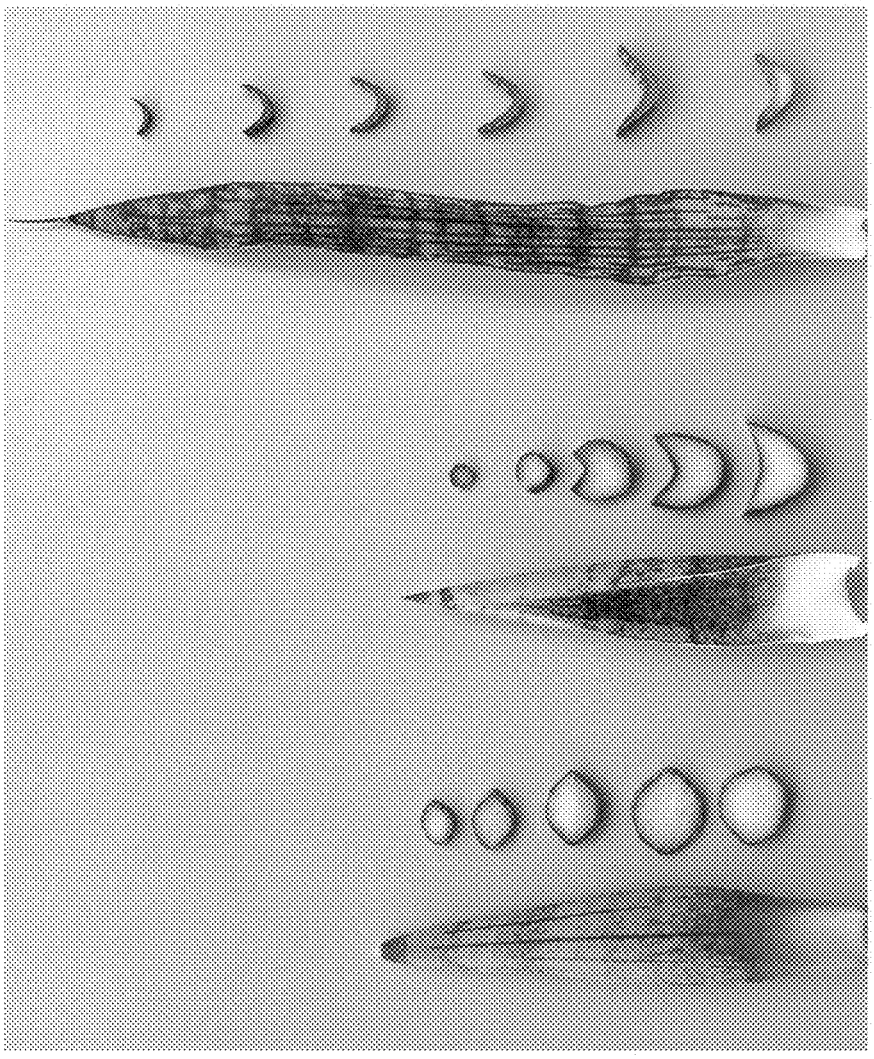

FIG. 8 Shows a comparison of adaxial leaf surfaces of 'HANSOTI61' (center) with the parent cultivar, 'Hedgehog' (left) and comparator 'Hansoti26' (right), accompanied by a width-wise slice of each leaf to illustrate the leaf shape and sulcus.

DETAILED BOTANICAL DESCRIPTION

The new *Sansevieria* 'HANSOTI61' has not been observed under all possible environmental conditions. The phenotype of the new cultivar may vary with variations in environment such as temperature, light intensity, fertilizer levels and composition and day length without any change in the genotype of the plant.

The aforementioned photographs, together with the following observations, measurements and values describe the new *Sansevieria* cultivar 'HANSOTI61' plants grown in an open poly house (high tunnel) at Village Asle, District Satara, Maharashtra State in Western India. Average temperature in Asle is 25° C., with summer highs of 39° C. and winter lows of 6° C. Plants grow under natural light conditions and between 30% to 75% shade levels depending on the season (higher shade in hot summer conditions).

This crop gets nearly constant fertilization to increase production. Controlled release fertilizer 13:11:11 Type 360-days release at 1 kilo/cubic meter of media, liquid fertilizer at approximately 100 ppm N, 20 ppm P and 100 ppm K, along with complete micronutrients. Production is closely related with proper and complete plant nutrition and an open soilless growing media based on coconut coir. The plants are grown in plastic pots on metal benching in spacing trays.

Color references are made to The Royal Horticultural Society Colour Chart (R.H.S.), 2007 ($5^{th}$ Edition), except where general colors of ordinary significance are used. It should be noted that colors in *Sansevieria* are somewhat variable depending on light levels, nutrition balance, age of plant and other factors. Plant & leaf size, width, thickness and color can vary considerably depending on light levels, feed composition and EC and pot size.

The photographs and descriptions were taken during the winter season in Asle, District Satara, Maharashtra State, India when outdoor day temperatures were 25° C. to 30° C. and nights, usually of 10° C. to 15° C. The age of the plants described is 3-4 months in 9 cm pots.

Botanical classification: *Sansevieria* hybrid 'HANSOTI61'.

General information:

*Parentage*.—Open pollinated seedling from a plant labelled as *Sansevieria* 'Hedgehog', an unusual *Sansevieria cylindrica* hybrid with an alternate phyllotaxy, giving a rosette of terete leaves rather than the usual Distichous phyllotaxy of typical *S. cylndrica* species and hybrids which present as a "fan" of leaves rather than a rosette (unpatented).

*Optimal growth conditions*.—High adaptability to outdoor or indoor conditions.

*Light intensities*.—High adaptability to outdoor or indoor conditions but needs some shade in hot climates.

*Temperature*.—Day: 25° C. to 35° C. Night: 15° C. to 25° C.

*Temperature tolerance*.—Tolerant to a low temperature of about 6° C. and a high temperature of 38° C. and above-very heat tolerant.

*Fertilization*.—Constant feed of 150 ppm N, 30 ppm P and 150 ppm K is used along with micronutrients with occasional leaching. Media incorporation of 13:11:11 Type 360 days release at 1 kg/cubic meter of media.

*Growth regulators*.—Not necessary for growing this cultivar.

Propagation:

*Typical*.—Vegetative, by leaf cuttings-unlike most *Sansevieria* cultivars, 'Hansoti61' comes true from leaf cuttings. Propagation using side shoots or suckers also possible but not used by us as plant shape is better from leaf cuttings.

*Rooting habit and description*.—Leaf cuttings root easily and subsequently gives adventitious pups from the cut edge of the leaf cutting.

*Time to initiate roots*.—30 to 40 days at 25° C. to 30° C.

*Time to produce a rooted liner*.—Additional 60 to 75 days at 25° C. to 30° C.

*Time to produce ready* 12 *cm potted plant from liner*.—About 3 months at 25° C. to 30° C.

Plant:

*General appearance and form*.—Monocot; leaf bases arranged in a rosette around growth point.

*Height*.—About 8 to 9 cm when grown in 9 cm pots.

*Spread*.—About 9 to 10 cm when grown when grown in a 9 cm size container.

*Rosette height* (*center*).—About 4 to 6 cm.

*Rosette diameter*.—About 9 to 10 cm.

*Growth habit*.—Upright.

*Shape*.—Inverted triangle.

*Fragrance*.—None.

*Stem*.—Modified rhizome which are fleshy with erect foliage. Texture: Smooth, waxy. Color: Greyed-Orange 164A. Strength: Strong and durable.

*Internode length*.—About 1 mm.

Foliage:

*Quantity*.—About 15 to 18 in ready to sell plant. Number increases with age.

*Arrangement and attachment*.—Rosulate; leaf bases arranged in a rosette around growth point.

*Leaf length*.—About 7 to 8 cm, in a plant finished in a 9 cm pot.

*Leaf width*.—About 1.5 to 1.7 cm, at widest point.

*Overall shape of leaf*.—Lanceolate.

*Apex shape*.—Acuminate and with somewhat stiff tip but safe to handle.

*Base shape*.—Decurrent.

*Margin*.—Entire.

*Texture*.—Upper Surface: Smooth and waxy texture.

*Texture*.—Under Surface: Smooth and waxy texture.

*Pubescence*.—None.

*Attachment*.—Sessile.

*Color of mature leaf*.—Because the leaves are held so upright, the most prominently visible surface of each leaf is, technically, the lower surface while the upper surface is mostly hidden inside the rosette.

*Lower surface*.—Basal silvery grey-green color near 190A with darker lines and cross hatching near 139A.

*Upper surface*.—Basal silvery grey-green colour near 191B or 191C with darker lines and cross hatching near 139A. With age the basal colour darkens slightly, nearer to 138A.

*Crossbanding*.—As typical for many *Sansevieria*, prominent, darker green annular rings, around 139A in colour, around leaf circumference.

*Venation pattern*.—Not visible on leaf surface. Longitudinal/parallel to leaf shape.

*Leaf fragrance*.—None.

Other:

*Inflorescence description*.—Flowers not observed to date.

*Weather resistance*.—Very drought tolerant.

*Pest resistance*.—Reasonably resistant to pests, susceptible to root mealybugs (*Rhizoecus pritchardi*). Typical pests include *Pseudococcidae longispinus* and *Tetranychus urticae*.

*Disease resistance*.—Shows resistance to Anthracnose. Largely disease-free from clean mother stock and appropriate disease mitigation measures undertaken.

*Fruit/seed production*.—No fruits/seeds detected to date.

What is claimed is:

1. A new and distinct cultivar of *Sansevieria* plant named 'HANSOTI61' as herein illustrated and described.

* * * * *